US00PP20266P2

(12) United States Plant Patent
Ivey

(10) Patent No.: US PP20,266 P2
(45) Date of Patent: Sep. 8, 2009

(54) ZOYSIAGRASS PLANT NAMED 'SHADOW TURF'

(50) Latin Name: *Zoysia matrella*
Varietal Denomination: Shadow Turf

(76) Inventor: Mark A. Ivey, 1318 E. Municipal Dr., Lubbock, TX (US) 79403

( * ) Notice: Subject to any disclaimer, the term of this patent is extended or adjusted under 35 U.S.C. 154(b) by 31 days.

(21) Appl. No.: 12/075,705

(22) Filed: Mar. 13, 2008

Related U.S. Application Data

(60) Provisional application No. 60/918,001, filed on Mar. 14, 2007.

(51) Int. Cl.
*A01H 5/00* (2006.01)

(52) U.S. Cl. ..... Plt./390
(58) Field of Classification Search ..... Plt./390
See application file for complete search history.

*Primary Examiner*—Susan B McCormick Ewoldt
(74) *Attorney, Agent, or Firm*—Penny J. Aguirre

(57) ABSTRACT

*Zoysia matrella* 'Shadow Turf', is a new and unique cultivar that is characterized by its ability to produce quality turf in shady conditions with deep green foliage, a moderate to vigorous growth habit, medium-fine texture, cold hardiness to U.S.D.A. Zone 6b and its adaptability in a wide range of growing conditions.

2 Drawing Sheets

Botanical classification: *Zoysia matrella.*
Varietal designation: 'Shadow Turf'.

BACKGROUND OF THE INVENTION

The present invention relates to a new and distinct cultivar of *Zoysia matrella* and will be referred to hereafter by its cultivar name, 'Shadow Turf'. 'Shadow Turf' represents a new cultivar of zoysiagrass for use as a turfgrass wherever zoysiagrass is adapted.

The inventor discovered the new cultivar, 'Shadow Turf', as a naturally occurring whole plant mutation at his nursery in Lubbock, Tex. in March 2005. The parentage of 'Shadow Turf' is unknown. 'Shadow Turf' was selected for its uniformity and performance in shady conditions and was subsequently evaluated in comparison trials and by DNA fingerprinting to further determine its uniqueness and its potential use as a turfgrass.

Asexual reproduction of the new cultivar was first accomplished by rooting stem cuttings that included stolons and rhizomes in Lubbock, Tex. in April 2005 by the inventor. The characteristics of this cultivar have been determined to be stable and are reproduced true to type in successive generations.

SUMMARY OF THE INVENTION

The following traits of the new cultivar have been repeatedly observed and in combination distinguish 'Shadow Turf' as a unique cultivar of zoysiagrass. 'Shadow Turf' has not been observed under all possible environmental conditions. The phenotype may vary somewhat with variations in temperature, day-length, light intensity, soil types, and water and fertility levels without, however, any variance in genotype. The measurements, observations, and descriptions that follow describe plants after 6 weeks and 12 weeks of greenhouse experiments and field trials in Lubbock, Tex. Performance in shady conditions was determined by growth under 50% and 90% light reducing cloth in a greenhouse.

1. 'Shadow Turf' produces quality turf in shady conditions.

2. 'Shadow Turf' exhibits deep green foliage that is retained when grown in shady conditions.
3. 'Shadow Turf' has a moderate to vigorous growth habit in comparison to other cultivars of zoysiagrass.
4. 'Shadow Turf' exhibits a medium-fine leaf texture.
5. 'Shadow Turf' has a unique DNA fingerprint when compared to 14 other zoysiagrass genotypes.
6. 'Shadow Turf' is cold hardy in U.S.D.A. Zone 6b.
7. 'Shadow Turf' is widely adaptable and tolerant to hot and dry conditions in full sun as well as shady conditions.

'Shadow Turf' was grown in comparison trials with other five cultivars of zoysiagrass; 'Zorro' (U.S. Plant Pat. No. 14,130), 'Meyer' (not patented), DALZ 0501 (not patented), 'Diamond' (U.S. Plant Pat. No. 10,636), and 'Emerald' (not patented). The closest comparison plants are *Zoysia* 'Diamond' (U.S. Plant Pat. No. 10,636) and *Zoysia* 'Emerald' (not patented). In comparison to 'Diamond', 'Shadow Turf', although similar in shade tolerance and leaf color, has a faster growth rate and a coarser leaf texture. In comparison to 'Emerald', 'Shadow Turf', although similar in leaf texture, has better shade tolerance and a more vigorous growth rate.

BRIEF DESCRIPTION OF THE DRAWING

The accompanying colored photographs illustrate the overall appearance and distinct characteristics of the new zoysiagrass.

Figure 1:
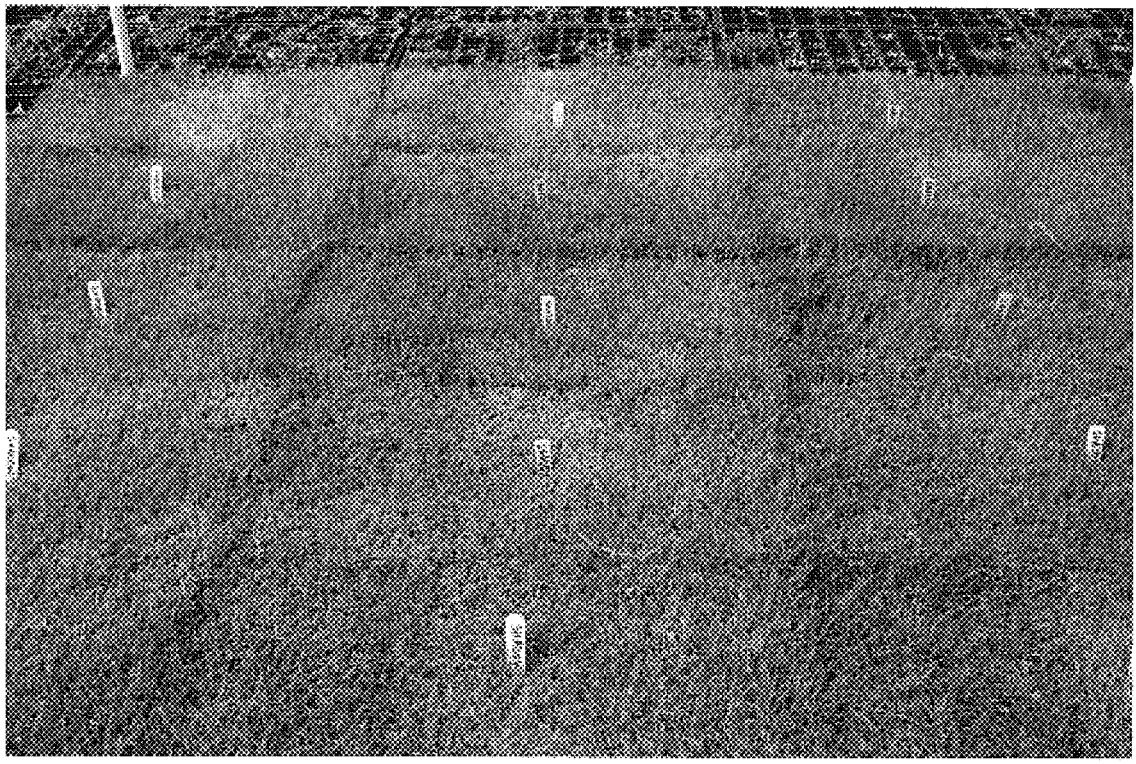
FIG. 1 shows a planting of 'Shadow Turf' as grown in 72-cell trays under greenhouse conditions for 2.5 months.
Figure 2:
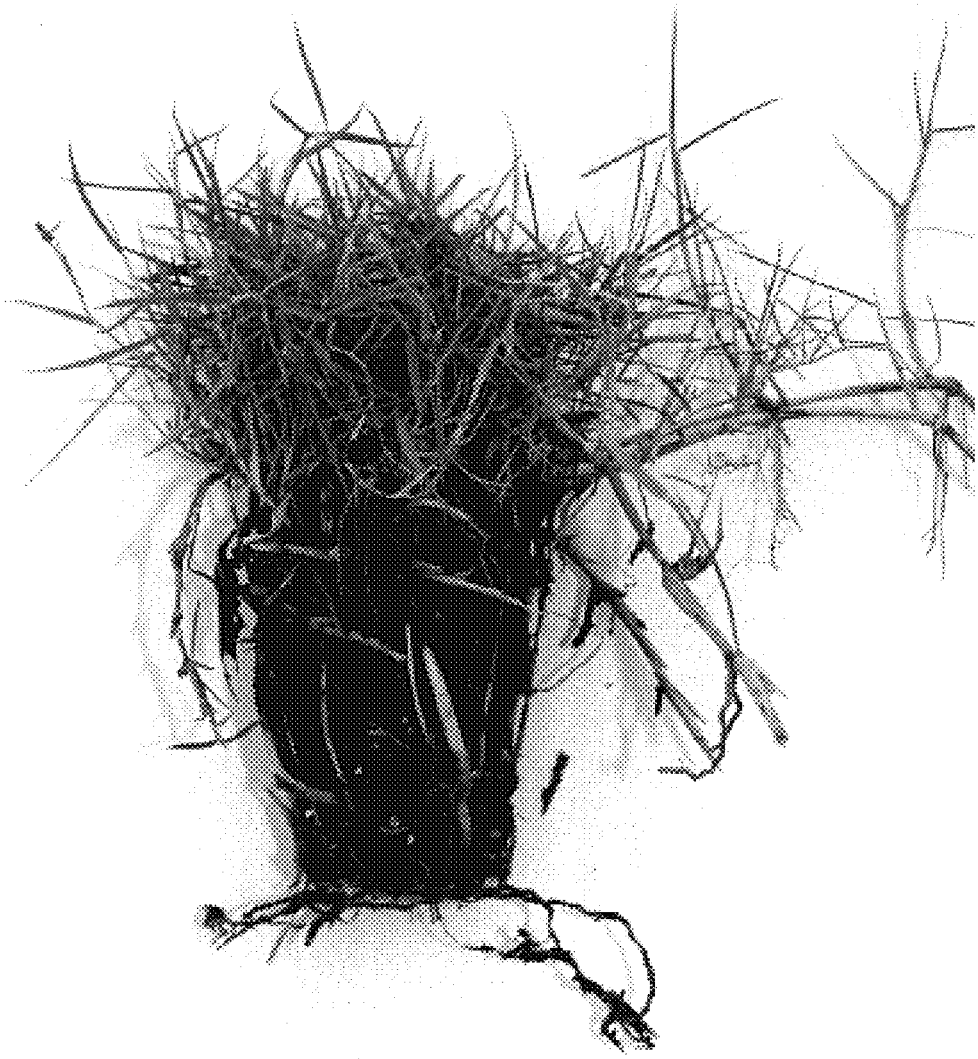

The photograph in FIG. 2 was taken of a 72-cell plug after 6 months of growth.

The colors in the photographs are as close as possible with the digital photography techniques available, the color values cited in the detailed botanical description accurately describe the colors of the new zoysiagrass.

COMPLETE DESCRIPTION OF THE PLANT

Field experiments were conducted in 2006 and 2007 to evaluate the relative growth and establishment rate of 'Shadow Turf' zoysiagrass compared to other zoysiagrass genotypes. Zoysiagrass genotypes were established using 10-$cm^2$ vegetative plugs and growth was monitored for 12 weeks. In 2006, 'Shadow Turf' exhibited the third highest initial increase in plug diameter (24 cm) 6 weeks after planting (WAP) (Table 1). Plug diameter of 'Shadow Turf' zoysiagrass 6 WAP in 2006 was similar to that of 'Meyer' (28 cm), DALZ 0501 (22 cm), and 'Emerald' (21 cm), lower than that of 'Zorro' (34 cm), and higher than that of 'Diamond' (18 cm) 6 WAP. In 2007, 'Shadow Turf' exhibited the second largest initial increase in plug diameter (19 cm) 6 WAP (Table 1). Growth of 'Shadow Turf' was similar to that of 'Zorro' (18 cm) and DALZ 0501 (18 cm) 6 WAP. 'Shadow Turf' exhibited a larger plug diameter than that of 'Emerald' (17 cm) and 'Diamond' (14 cm), but was less than that of 'Meyer' (22 cm) 6 WAP. In 2006, 'Shadow Turf' exhibited the third largest plug diameter (36 cm) 12 WAP (Table 1). Growth of 'Shadow Turf' was similar to that of DALZ 0501 (30 cm), greater than that of 'Emerald' (27 cm) and 'Diamond' (23 cm), but less than that of 'Zorro' (49 cm) and 'Meyer' (48 cm) 12 WAP. In 2007, 'Shadow Turf' exhibited the third highest increase in plug diameter (57 cm) 12 WAP (Table 1). Plug diameter of 'Shadow Turf' was similar to that of 'Meyer' (60 cm), 'Zorro' (59 cm), and DALZ 0501 (53 cm) and greater than that of 'Emerald' (42 cm) and 'Diamond' (38 cm) 12 WAP.

Field experiments were conducted in 2007 to evaluate the relative turfgrass color of 'Shadow Turf' zoysiagrass compared to other zoysiagrass genotypes. Zoysiagrass genotypes were established using 10-$cm^2$ vegetative plugs and turfgrass color was monitored for 12 weeks. Turfgrass color was visually estimated on a scale of 1 (brown turf) to 9 (dark green). 'Shadow Turf' exhibited the highest turfgrass color rating (7.5) of all zoysiagrass genotypes evaluated 6 WAP (Table 2). Turfgrass color of 'Shadow Turf' zoysiagrass was similar to that of 'Diamond' (7.3), DALZ 0501 (7.3), 'Emerald' (7.0), and 'Zorro' (6.8), and greater than 'Meyer' (6.3) 6 WAP. 'Shadow Turf' exhibited the third highest turfgrass color rating (7.3) 12 WAP (Table 2). Turfgrass color of 'Shadow Turf' zoysiagrass was similar to 'Diamond' (7.8), DALZ 0501 (7.0), 'Meyer' (7.0), and 'Zorro' (6.8), but was lower than 'Emerald' (8.0) 12 WAP.

Greenhouse experiments were conducted in 2006 and 2007 to evaluate the relative effect of three shade levels (0%, 50%, and 90% shade) on the growth of 'Shadow Turf' zoysiagrass compared to other zoysiagrass genotypes. Plugs (2.5-$cm^2$) of each genotype were planted in pots and placed under artificial shade cloth canopies. Growth was expressed as the percent plug diameter increase for each genotype, and recorded for 12 weeks. In 2006, 'Shadow Turf' exhibited the second highest increase in plug diameter (36%) 6 WAP when grown under 50% shade (Table 3). 'Shadow Turf' growth was similar to 'Diamond' (38%), 'Zorro' (34%), and 'Meyer' (33%), and greater than DALZ 0501 (21%) and 'Emerald' (19%) 6 WAP when grown under 50% shade. 'Shadow Turf' exhibited the highest percent increase in plug diameter (18%) 6 WAP when grown under 90% shade (Table 3). Growth under 90% shade of 'Shadow Turf' was similar to 'Diamond' (18%), DALZ 0501 (18%), and 'Emerald' (18%), and greater than 'Zorro' (−38%) and 'Meyer' (−49%) 6 WAP. In 2007, 'Shadow Turf' exhibited the second highest increase in plug diameter (40%) 6 WAP when grown under 50% shade (Table 3). 'Shadow Turf' growth was similar to that of 'Diamond' (41%), but greater than DALZ 0501 (29%), 'Emerald' (29%), 'Meyer' (24%), and 'Zorro' (16%) 6 WAP when grown under 50% shade. 'Shadow Turf' exhibited the second highest increase in plug diameter (10%) 6 WAP when grown under 90% shade (Table 3). Growth of 'Shadow Turf' was similar to 'Diamond' (10%) and DALZ 0501 (14%), but greater than 'Meyer' (6%), 'Emerald' (−2%), and 'Zorro' (−3%) 6 WAP when grown under 90% shade. In 2006, 'Shadow Turf' zoysiagrass exhibited the second highest increase in plug diameter (68%) when grown under 50% shade 12 WAP (Table 4). Growth of 'Shadow Turf' was similar to that of 'Diamond' (69%), but greater than 'Meyer' (56%), 'Zorro' (40%), DALZ 0501 (37%), and 'Emerald' (28%) 12 WAP when grown under 50% shade. 'Shadow Turf' exhibited the greatest increase in plug diameter (21%) 12 WAP when grown under 90% shade (Table 4). Growth was similar to DALZ 0501 (15%) and 'Diamond' (5%), but greater than 'Emerald' (−31%), 'Zorro' (−55%), and 'Meyer' (−87%) 12 WAP when grown under 90% shade. In 2007, 'Shadow Turf' zoysiagrass exhibited the largest increase in plug diameter (60%) 12 WAP when grown under 50% shade (Table 4). Growth of 'Shadow Turf' was similar to 'Diamond' (60%), but greater than 'Emerald' (49%), DALZ 0501 (48%), 'Meyer' (24%), and 'Zorro' (21%) 12 WAP when grown under 50% shade. 'Shadow Turf' exhibited the greatest increase in plug diameter (11%) 12 WAP when grown under 90% shade (Table 4). Growth of 'Shadow Turf' zoysiagrass was similar to 'Diamond' (11%) and DALZ 0501 (7%), but greater than 'Meyer' (−17%), 'Emerald' (−21%), and 'Zorro' (−38%) 12 WAP when grown under 90% shade.

Greenhouse experiments were conducted in 2006 and 2007 to evaluate the relative effect of three shade levels (0, 50%, and 90% shade) on the performance of 'Shadow Turf' zoysiagrass to other zoysiagrass genotypes. Plugs (2.5-$cm^2$) of each genotype were planted in pots and placed under artificial shade cloth canopies. Turfgrass quality was visually estimated on a scale of 1 (dead turf) to 9 (ideal turf) for 12 weeks. In 2006, 'Shadow Turf' exhibited the greatest turfgrass quality (5.7) 12 WAP when grown under 50% shade (Table 5). Turfgrass quality of 'Shadow Turf' zoysiagrass was similar to 'Diamond' (5.0), 'Meyer' (5.0), and 'Zorro' (5.0), but greater than 'Emerald' (4.3) and DALZ 0501 (4.3) 12 WAP when grown under 50% shade. 'Shadow Turf' exhibited the greatest turfgrass quality (4.7) 12 WAP when grown under 90% shade. Turfgrass quality of 'Shadow Turf' zoysiagrass was similar to 'Diamond' (3.7), and greater than 'Emerald' (1.7), DALZ 0501 (1.7), 'Zorro' (1.3), and 'Meyer' (1.0) 12 WAP when grown under 90% shade. In 2007, 'Shadow Turf' exhibited the second highest turfgrass quality (6.3) 12 WAP when grown under 90% shade (Table 5). Turfgrass quality of 'Shadow Turf' was similar to the remaining zoysiagrass genotypes with turfgrass quality ratings of 5.0 to 5.3 12 WAP when grown under 50% shade. 'Shadow Turf' zoysiagrass exhibited the greatest turfgrass quality (5.3) 12 WAP when grown under 90% shade. Turfgrass quality of 'Shadow Turf' was similar to 'Diamond' (5.3) and DALZ 0501 (4.7), but greater than 'Emerald' (3.0), 'Meyer' (2.3), and 'Zorro' (2.0) 12 WAP when grown under 90% shade.

Greenhouse experiments were conducted in 2006 and 2007 to evaluate the relative effect of three shade levels (0%, 50%, and 90% shade) on the performance of 'Shadow Turf' zoysiagrass to other zoysiagrass genotypes. Plugs (2.5-$cm^2$) of each genotype were planted in pots and placed under artificial shade cloth canopies. Turfgrass color was visually estimated on a scale of 1 (dead turf) to 9 (ideal turf) for 12 weeks. In 2006, 'Shadow Turf' zoysiagrass exhibited the second greatest turfgrass color (6.3) 12 WAP when grown under 50% shade (Table 6). No differences were observed in turfgrass color of 'Shadow Turf' and the remaining zoysiagrass genotypes 12 WAP when grown under 50% shade. 'Shadow Turf' zoysiagrass exhibited the greatest turfgrass color (6.0) 12 WAP when grown under 90% shade. Turfgrass color of 'Shadow Turf' zoysiagrass was greater than all other zoysiagrass genotypes, which exhibited turfgrass color ratings of 1.0 to 4.0. In 2007, 'Shadow Turf' exhibited the second greatest turfgrass color (7.0) 12 WAP when grown under 50% shade (Table 6). Turfgrass color of 'Shadow Turf' zoysiagrass was similar to 'Diamond' (7.7), 'Emerald' (7.0), 'Meyer' (6.3), and 'Zorro' (6.0) 12 WAP when grown under 50% shade. 'Shadow Turf' exhibited the second highest turfgrass color rating (5.3) 12 WAP when grown under 90% shade. Turfgrass color of 'Shadow Turf' zoysiagrass was similar to 'Diamond' (6.3), 'Emerald' (4.0), DALZ 0501 (3.7), and 'Meyer' (3.0) 12 WAP when grown under 90% shade.

TABLE 1

Mean plug diameter (cm) of six zoysiagrass genotypes 6 and 12 WAP established in 2006 and 2007.

| | Plug Diameter | | | |
|---|---|---|---|---|
| | 6 WAP | | 12 WAP | |
| Genotype | 2006 | 2007 | 2006 | 2007 |
| | cm | | | |
| 'Zorro' | 34 a† | 18 bc | 49 a | 59 a |
| 'Meyer' | 28 b | 22 a | 48 a | 60 a |
| 'Shadow Turf' | 24 bc | 19 b | 36 b | 57 ab |
| DALZ 0501 | 22 cd | 18 bc | 30 bc | 53 b |
| 'Emerald' | 21 cd | 17 c | 27 c | 42 c |
| 'Diamond' | 18 d | 14 d | 23 c | 38 c |

†Means within a column followed by the same lower case letter are not significantly different at P ± 0.05 according to Fisher's Protected LSD test.

TABLE 2

Mean turfgrass color of six zoysiagrass genotypes 6 and 12 WAP established in 2007.

| | Turfgrass Color | |
|---|---|---|
| Genotype | 6 WAP | 12 WAP |
| | (1-9) | |
| 'Shadow Turf' | 7.5 a† | 7.3 bc |
| 'Diamond' | 7.3 a | 7.8 ab |
| 'Emerald' | 7.0 ab | 8.0 a |
| DALZ 0501 | 7.3 a | 7.0 c |
| 'Zorro' | 6.8 ab | 6.8 c |
| 'Meyer' | 6.3 b | 7.0 c |

†Means within a column followed by the same lower case letter are not significantly different at P ± 0.05 according to Fisher's Protected LSD test.

TABLE 3

Percent plug diameter increase of six zoysiagrass genotypes when exposed to 0%, 50%, and 90% shade 6 WAP.

| | Plug Diameter Increase 6 WAP | | | | | |
|---|---|---|---|---|---|---|
| | 2006 Shade Level | | | 2007 Shade Level | | |
| Genotype | 0 | 50 | 90 | 0 | 50 | 90 |
| | % | | | | | |
| 'Shadow Turf' | 68 | 36 | 18 | 74 | 40 | 10 |
| 'Diamond' | 52 | 38 | 18 | 52 | 41 | 10 |
| DALZ 0501 | 49 | 21 | 18 | 64 | 29 | 14 |
| 'Emerald' | 68 | 19 | 18 | 47 | 29 | −2 |
| 'Zorro' | 47 | 34 | −38 | 32 | 16 | −3 |
| 'Meyer' | 55 | 33 | −49 | 49 | 24 | 6 |
| LSD | 35 | 35 | 35 | 22 | 22 | 22 |

TABLE 4

Percent plug diameter increase of six zoysiagrass genotypes when exposed to 0%, 50%, and 90% shade 12 WAP.

| | Plug Diameter Increase 12 WAP | | | | | |
|---|---|---|---|---|---|---|
| | 2006 Shade Level | | | 2007 Shade Level | | |
| Genotype | 0 | 50 | 90 | 0 | 50 | 90 |
| | % | | | | | |
| 'Shadow Turf' | 88 | 68 | 21 | 114 | 60 | 11 |
| 'Diamond' | 124 | 69 | 5 | 89 | 60 | 11 |
| DALZ 0501 | 84 | 37 | 15 | 107 | 48 | 7 |
| 'Emerald' | 78 | 28 | −31 | 91 | 49 | −21 |
| 'Zorro' | 53 | 40 | −55 | 79 | 21 | −38 |
| 'Meyer' | 103 | 56 | −87 | 72 | 24 | −17 |
| LSD | 33 | 33 | 33 | 25 | 25 | 25 |

TABLE 5

Turfgrass quality of six zoysiagrass genotypes when exposed to 0%, 50%, and 90% shade 12 WAP.

| | Turfgrass Quality 12 WAP | | | | | |
|---|---|---|---|---|---|---|
| | 2006 Shade Level | | | 2007 Shade Level | | |
| Genotype | 0 | 50 | 90 | 0 | 50 | 90 |
| | (1-9) | | | | | |
| 'Diamond' | 7.0 | 5.0 | 3.7 | 7.0 | 7.0 | 5.3 |
| 'Shadow Turf' | 7.0 | 5.7 | 4.7 | 7.0 | 6.3 | 5.3 |
| 'Emerald' | 6.7 | 4.3 | 1.7 | 5.7 | 5.3 | 3.0 |
| DALZ 0501 | 6.7 | 4.3 | 1.7 | 7.0 | 5.0 | 4.7 |
| 'Zorro' | 5.7 | 5.0 | 1.3 | 6.0 | 5.3 | 2.0 |
| 'Meyer' | 6.3 | 5.0 | 1.0 | 6.0 | 5.0 | 2.3 |
| $LSD_{0.05}$ | 1.1 | 1.1 | 1.1 | 1.3 | 1.3 | 1.3 |

TABLE 6

Turfgrass color of six zoysiagrass genotypes when exposed to 0%, 50%, and 90% shade 12 WAP.

| | Turfgrass Color 12 WAP | | | | | |
|---|---|---|---|---|---|---|
| | 2006 Shade Level | | | 2007 Shade Level | | |
| Genotype | 0 | 50 | 90 | 0 | 50 | 90 |
| | (1-9) | | | | | |
| 'Diamond' | 8.0 a† | 6.7 a | 4.0 b | 8.0 a | 7.7 a | 6.3 a |
| 'Shadow Turf' | 6.7 b | 6.3 a | 6.0 a | 7.7 ab | 7.0 ab | 5.3 ab |

TABLE 6-continued

Turfgrass color of six zoysiagrass genotypes when exposed to 0%, 50%, and 90% shade 12 WAP.

| Genotype | Turfgrass Color 12 WAP | | | | | |
|---|---|---|---|---|---|---|
| | 2006 Shade Level | | | 2007 Shade Level | | |
| | 0 | 50 | 90 | 0 | 50 | 90 |
| | (1-9) | | | | | |
| 'Emerald' | 6.7 b | 6.3 a | 1.7 c | 7.3 ab | 7.0 ab | 4.0 abc |
| DALZ 0501 | 6.7 b | 6.3 a | 1.7 c | 7.0 b | 5.7 c | 3.7 bc |
| 'Zorro' | 6.7 b | 6.0 a | 1.3 c | 7.0 b | 6.0 bc | 2.3 c |
| 'Meyer' | 6.7 b | 6.3 a | 1.0 c | 7.0 b | 6.3 bc | 3.0 bc |

†Means within a column followed by the same lower case letter are not significantly different at P ± 0.05 according to Fisher's Protected LSD test.

COMPLETE BOTANICAL DESCRIPTION OF THE PLANT

The following is a detailed description of the new cultivar as grown in a greenhouse with an average temperature of 80° F. for 6 months. The color determination is in accordance with the 2001 R.H.S. Colour Chart of The Royal Horticultural Society, London, England, except where general color terms of ordinary dictionary significance are used.

General description:

*Plant habit.*—Perennial, spreads by stolons and rhizomes to produce a dense turfgrass.

*Hardiness.*—U.S.D.A. Zone 6b.

*Culture.*—Adaptable, grows well and retains leaf color in hot dry conditions in full sun as well as in shady conditions.

*Diseases and pests.*—No susceptibility or resistance to diseases or pests that affect zoysiagrass has been observed.

*Root description.*—Fibrous roots on rhizomes.

Growth and propagation:

*Propagation.*—Stem cuttings of sections including stolon and rhizome.

*Time required for root production.*—30 days in a greenhouse with an ambient temperature of approximately 80° F. without bottom heat.

*Time required for root development.*—90 to 180 days to finish a 1¾ inch plug depending on environmental conditions at the time of propagation.

Stolon description:

*Stolon color.*—146C maturing to 164C.

*Internode length.*—Average of 1.9 cm.

*Roots.*—Fibrous, 164C in color.

Foliage description:

*Leaf texture.*—Medium-fine.

*Leaf blade shape.*—Linear, rolled into bud on emergence, concavely.

*Leaf blade base.*—Sheathed.

*Leaf blade surface.*—Smooth, slightly glaucous.

*Leaf blade margin.*—Very fine, short hairs.

*Leaf apex.*—Tapering to a sharp point.

*Leaf blade veins.*—Parallel.

*Leaf bald aspect.*—Concave.

*Leaf size.*—Vegetative leaf, third youngest leaf; ranges from 1.5 to 4 cm in length and 1 mm in width, flag leaf; an average of 3.64 mm in length and 0.57 mm in width.

*Leaf blade flexibility* (*softness*).—Moderate.

*Sheath length.*—Ranges from 0.5 cm to 1.5 cm.

*Sheath color.*—144D to 144C.

*Ligule.*—Row of very fine silky hairs about 1.5 cm in length with leaf collar translucent and 144D in color.

*Leaf blade color* (*abaxial and adaxial surface*).—137C to 137B.

Inflorescence description:

*General description.*—Terminal spike-like raceme, with spikelets on short pedicels.

*Raceme size.*—Approximately 1.8 cm in length and up to 0.5 cm in width.

*Culm.*—Typically 3 to 4 cm in length to base of flag leaf, 144B in color.

*Spikelet length.*—About 4 mm.

*Reproductive organs.*—Anthers; 2 to 3, about 1.2 mm in length, 144D in color, versatile attachment, Pistil; 1, 2 plumose stigmas about 1.6 cm in length and 161A in color.

*Seed.*—Seed development has not been observed to date.

It is claimed:

1. A new and distinct cultivar of zoysiagrass plant named 'Shadow Turf' as herein illustrated and described.

* * * * *